United States Patent
Gilson et al.

(10) Patent No.: US 10,561,443 B2
(45) Date of Patent: Feb. 18, 2020

(54) IMAGE-GUIDED EMBRYO TRANSFER FOR IN VITRO FERTILIZATION

(71) Applicants: Siemens Healthcare GmbH, Erlangen (DE); The Johns Hopkins University, Baltimore, MD (US)

(72) Inventors: Wesley David Gilson, North Beach, MD (US); Jan Fritz, Baltimore, MD (US)

(73) Assignees: Siemens Healthcare GmbH, Erlangen (DE); The Johns Hopkins University, Baltimore, MD (US)

( * ) Notice: Subject to any disclaimer, the term of this patent is extended or adjusted under 35 U.S.C. 154(b) by 464 days.

(21) Appl. No.: 15/541,623

(22) PCT Filed: Jun. 5, 2015

(86) PCT No.: PCT/US2015/034392
§ 371 (c)(1),
(2) Date: Jul. 5, 2017

(87) PCT Pub. No.: WO2016/195707
PCT Pub. Date: Dec. 8, 2016

(65) Prior Publication Data
US 2017/0340354 A1 Nov. 30, 2017

(51) Int. Cl.
*A61B 17/435* (2006.01)
*A61B 34/20* (2016.01)
(Continued)

(52) U.S. Cl.
CPC ............ *A61B 17/435* (2013.01); *A61B 5/055* (2013.01); *A61B 34/20* (2016.02); *A61B 90/37* (2016.02);
(Continued)

(58) Field of Classification Search
CPC ....... A61B 17/435; A61B 90/37; A61B 5/055; A61B 34/20; A61B 2090/364; A61B 2034/105; A61B 2090/365; A61B 2090/367; A61B 2090/3958; A61B 2034/107; A61B 2090/374; A61B 2034/2051; A61M 25/0127; G01R 33/287
See application file for complete search history.

(56) References Cited

U.S. PATENT DOCUMENTS

2004/0106869 A1* 6/2004 Tepper ................ A61B 8/0833
600/443
2005/0261546 A1 11/2005 Gergely et al.
(Continued)

OTHER PUBLICATIONS

International Search Report dated Mar. 8, 2016 in corresponding International Application No. PCT/US2015/034392.

*Primary Examiner* — Sanjay Cattungal (57) ABSTRACT

A method for performing image-guided embryo transfer for in vitro fertilization includes performing a pre-operative magnetic resonance imaging (MRI) scan of a subjects pelvic region to yield a first MRI image dataset. A computer applies a segmentation routine to the first MRI image dataset to yield segment data which is then used by the computer to create an anatomical model of the subjects pelvic region. The computer determines an optimal implant location based on the anatomical model and creates a three-dimensional rendering of the optimal implant location based on the first MRI image dataset.

15 Claims, 4 Drawing Sheets

(51) Int. Cl.
*A61B 90/00* (2016.01)
*A61B 5/055* (2006.01)
*A61M 25/01* (2006.01)
*G01R 33/28* (2006.01)
*A61B 34/10* (2016.01)

(52) U.S. Cl.
CPC ....... *A61M 25/0127* (2013.01); *G01R 33/287* (2013.01); *A61B 2034/105* (2016.02); *A61B 2034/107* (2016.02); *A61B 2034/2051* (2016.02); *A61B 2090/364* (2016.02); *A61B 2090/365* (2016.02); *A61B 2090/367* (2016.02); *A61B 2090/374* (2016.02); *A61B 2090/3958* (2016.02)

(56) References Cited

U.S. PATENT DOCUMENTS

| | | | |
|---|---|---|---|
| 2007/0208213 A1* | 9/2007 | Swann | A61B 17/435 600/33 |
| 2010/0268067 A1* | 10/2010 | Razzaque | A61B 34/20 600/424 |
| 2010/0312094 A1 | 12/2010 | Guttman et al. | |
| 2011/0137156 A1 | 6/2011 | Razzaque et al. | |
| 2013/0053657 A1* | 2/2013 | Ziarno | A61B 1/00016 600/304 |
| 2018/0250032 A1* | 9/2018 | Hildebrandt | A61B 8/12 |
| 2019/0247130 A1* | 8/2019 | State | A61B 8/4245 |

* cited by examiner

IMAGE-GUIDED EMBRYO TRANSFER FOR IN VITRO FERTILIZATION

TECHNOLOGY FIELD

The present invention relates generally to methods, systems, and apparatuses for using Magnetic Resonance Imaging (MRI) to perform image-guided embryo transfer for in vitro fertilization procedures.

BACKGROUND

Embryo transfer is the last step in the in vitro fertilization process. A proper transfer is critical to the success of the procedure. This is a delicate process and requires placement of the embryos in the most appropriate location of the endometrial cavity while minimizing trauma and unnecessary manipulation of the uterine milieu.

2D Ultrasound is currently considered the most effective technique for guiding the embryo transfer. Briefly, the physician inserts an embryo-loaded catheter through the cervical opening up into the middle of the uterus under ultrasound guidance. Continuous visibility of the catheter is frequently difficult as the catheter tip can get out of plane with the 2D ultrasound. Extensive research has determined that the optimal location for embryo placement is in the middle of the endometrial cavity—halfway from the internal cervix surface to the uterine fundus. The catheter should be positioned between the top and bottom layers of the endometrium with care taken not to dissect the endometrial surface, as sub-endometrial transfers result in lower success rates. Although considered to be the best guidance method, visualization of the critical structures can be difficult.

Recently, 3D/4D ultrasound has been introduced and has begun to be used in a number of sites. It provides improved visualization of the underlying anatomy for planning. However, image quality is still less than ideal for these procedures and is sonographer-dependent.

SUMMARY

Embodiments of the present invention address and overcome one or more of the above shortcomings and drawbacks, by providing methods, systems, and apparatuses related to using Magnetic Resonance Imaging (MRI) to perform image-guided embryo transfer for in vitro fertilization. The proposed technology provides several benefits over conventional ultrasound techniques, including the ability to identify and visualize optimal implant location with greater accuracy.

According to some embodiments of the present invention, a method for performing image-guided embryo transfer for in vitro fertilization includes performing a pre-operative magnetic resonance imaging (MRI) scan of a subject's pelvic region to yield a first MRI image dataset. A computer applies a segmentation routine to the first MRI image dataset to yield segment data which is then used by the computer to create an anatomical model of the subject's pelvic region. The computer determines an optimal implant location based on the anatomical model and creates a three-dimensional rendering of the optimal implant location based on the first MRI image dataset.

Additional features may be added to the aforementioned method in different embodiments. For example, in some embodiments, a real-time MRI scan of the subject's pelvic region is performed to yield a second MRI image dataset. The second MRI image dataset is next combined with the three-dimensional rendering of the optimal implant location (e.g., using an image fusion technique) to yield a combined image dataset. In some embodiments, a display is presented of the combined image dataset to guide insertion of a catheter into the subject's endometrial cavity for embryo transfer. Additionally, a visualization of the catheter may be presented on the display based on a radio frequency signal emitted by the catheter. For example, the visualization of the catheter on the display may be based on a detection of one or more paramagnetic rings included with the catheter.

In some embodiments of the aforementioned method, the three-dimensional rendering of the optimal implant location comprises a mesh centered at the optimal implant location. In this rendering, voxels corresponding to the optimal implant location may be presented with a different color representation than other voxels included in the mesh. Alternatively (or additionally), the voxels corresponding to the optimal implant location may be presented with a different opacity representation than other voxels included in the mesh.

According to other embodiments of the present invention, an article of manufacture comprising a computer-readable, non-transitory medium holds computer-executable instructions for performing the aforementioned method (with or without the various additional features noted above).

According to other embodiments of the present invention, a system for performing image-guided embryo transfer for in vitro fertilization includes an imaging device and a central control computer. The imaging device comprises a plurality of coils configured to acquire a first magnetic resonance imaging (MRI) image dataset representative of a subject's pelvic region acquired using a pre-operative MRI scan. The central control computer unit is configured to: apply a segmentation routine to the first MRI image dataset to yield segment data, create an anatomical model of the subject's pelvic region using the segment data, determine an optimal implant location based on the anatomical model, and create a three-dimensional rendering of the optimal implant location based on the first MRI image dataset.

In some embodiments of the aforementioned system, the imaging device is further configured to acquire a second MRI image dataset representative of the subject's pelvic region using a real-time MRI scan. In these embodiments, the central control computer unit may then be configured to combine the second MRI image dataset with the three-dimensional rendering of the optimal implant location to yield a combined image dataset. Then, the central control computer may be configured to present the combined image dataset on a display to guide insertion of a catheter into the subject's endometrial cavity for embryo transfer.

Various techniques may be used for creating the three-dimensional rendering of the optimal implant location in the aforementioned system. For example, in some embodiments, the three-dimensional rendering comprises a mesh centered at the optimal implant location and the central control computer is further configured to apply a first color value to a first group of voxels corresponding to the optimal implant location in the mesh and apply a distinct second color value to a second group of voxels corresponding to voxels in the mesh not included in the first group. Additionally, similar to the method described above, in some embodiments of the system, the central control computer unit is configured to present a visualization of the catheter on the display based on detection of a radio frequency signal emitted by the catheter and/or paramagnetic rings on the catheter.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses related to using Magnetic Resonance Imaging (MRI) to perform image-guided embryo transfer for in vitro fertilization. Using the techniques described herein, there is an opportunity to increase the efficiency of embryo transfers, thereby improving the success rate of single embryo transfer, reducing the need for multi-embryo transfers and reducing the need for multiple attempts at embryo transfer. One benefit of MRI is that the deployed embryo may be visualized in the uterine cavity using high spatial resolution T2-weighted MR imaging. This is in distinction to ultrasound, with which it is difficult to visualize this process. Moreover, although the examples described herein are all directed to embryo transfer, it should be noted that the various techniques described herein may be generalized and applied to other image-guided interventional medical procedure.

Figure 1:
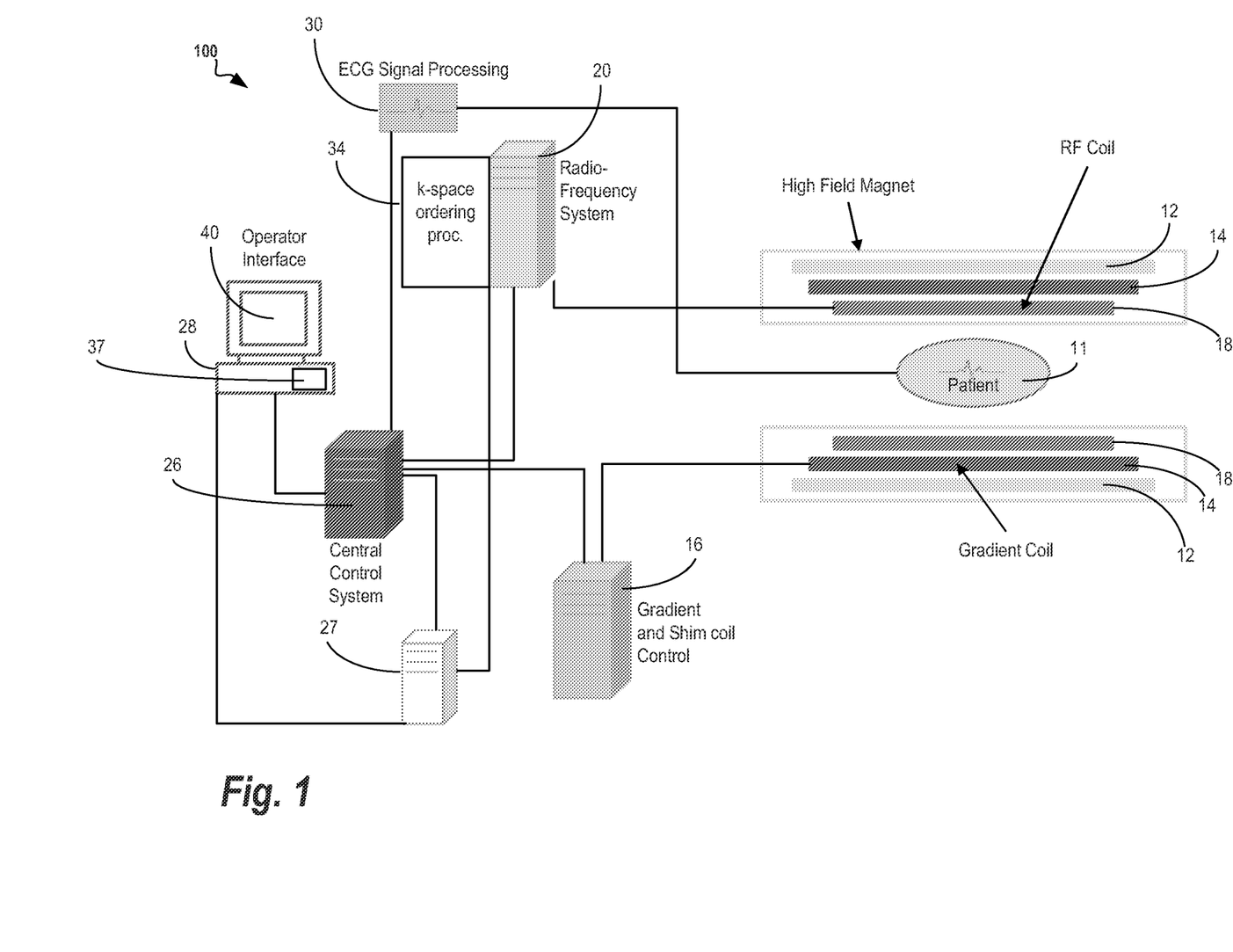
FIG. 1 shows a system for ordering acquisition of frequency domain components representing magnetic resonance image data for storage in a k-space storage array, as used by some embodiments of the present invention.

FIG. 1 shows a system 100 for ordering acquisition of frequency domain components representing MRI data for storage in a k-space storage array, as used by some embodiments of the present invention. In system 100, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MRI device magnetic field resulting from patient anatomical variation and other sources. The magnetic field gradients include a slice-selection gradient magnetic field, a phase-encoding gradient magnetic field and a readout gradient magnetic field that are applied to patient 11.

Further radio frequency (RF) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives magnetic resonance signals, i.e., signals from the excited protons within the body as they return to an equilibrium position established by the static and gradient magnetic fields. The magnetic resonance signals are detected and processed by a detector within RF module 20 and k-space component processor unit 34 to provide a magnetic resonance dataset to an image data processor for processing into an image. In some embodiments, the image data processor is located in central control unit 26. However, in other embodiments such as the one depicted in FIG. 1, the image data processor is located in a separate unit 27. ECG synchronization signal generator 30 provides ECG signals used for pulse sequence and imaging synchronization. A two or three dimensional k-space storage array of individual data elements in k-space component processor unit 34 stores corresponding individual frequency components comprising a magnetic resonance dataset. The k-space array of individual data elements has a designated center and individual data elements individually have a radius to the designated center.

A magnetic field generator (comprising coils 12, 14, and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components is sequentially acquired during acquisition of a magnetic resonance dataset representing an magnetic resonance image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components is substantially minimized.

Central control unit 26 uses information stored in an internal database to process the detected magnetic resonance signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging.

Generated images are presented on display 40 of the operator interface. Computer 28 of the operator interface includes a graphical user interface (GUI) enabling user interaction with central control unit 26 and enables user modification of magnetic resonance imaging signals in substantially real time. Continuing with reference to FIG. 1, display processor 37 processes the magnetic resonance signals to reconstruct one or more images for presentation on display 40, for example. Various techniques may be used for reconstruction. For example, in conventional systems, an optimization algorithm is applied to iteratively solve a cost function which results in the reconstructed image.

Figure 2:
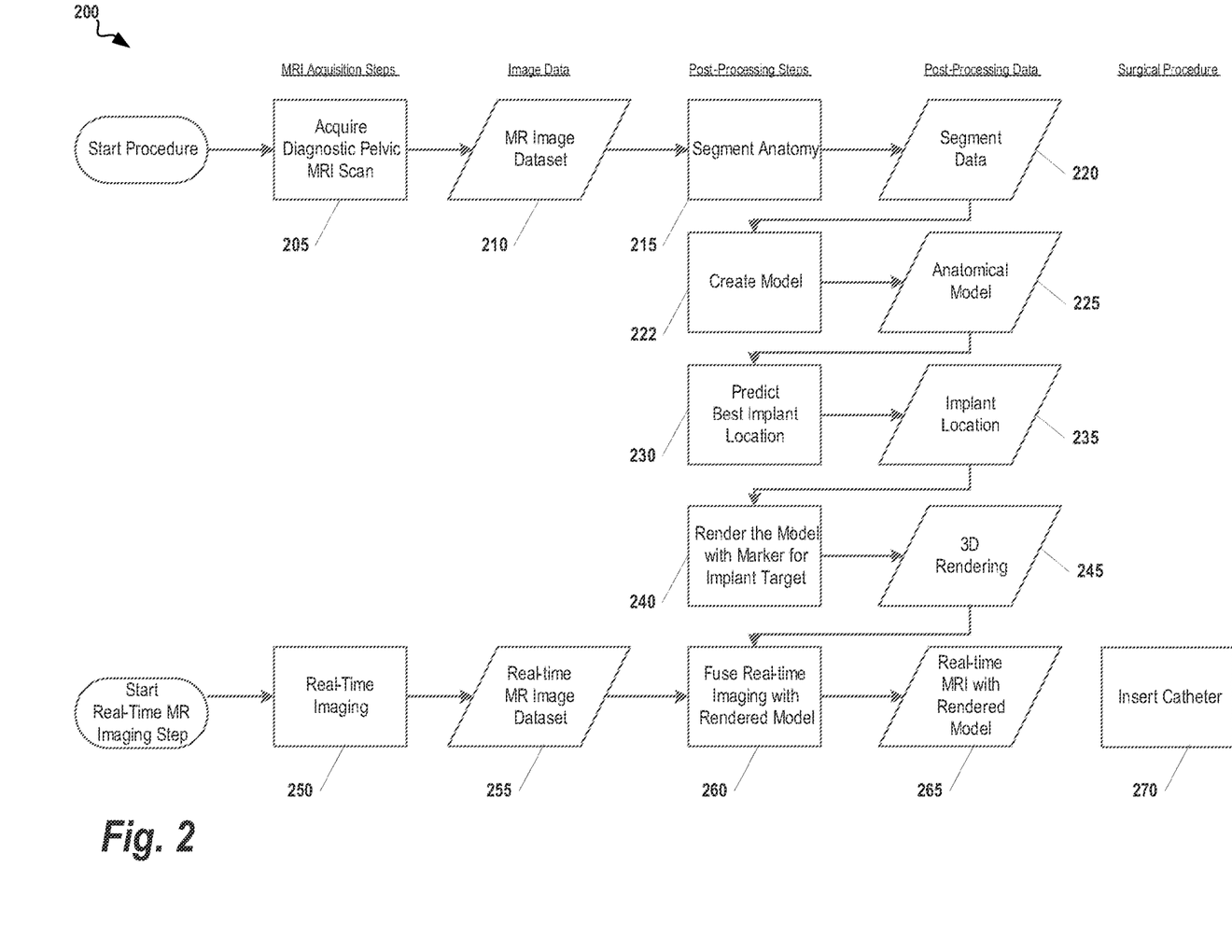
FIG. 2 provides an overview of a process for image-guided embryo transfer for in vitro fertilization, according to some embodiments.

FIG. 2 provides an overview of a process 200 for image-guided embryo transfer for in vitro fertilization, according to some embodiments. The method begins at step 205 with the acquisition of conventional diagnostic MR images of the subject's pelvis during a pre-operative procedure. These images may be acquired, for example, using the system 100 illustrated in FIG. 1. A high resolution, isotropic (or near isotropic) image dataset is preferred with good signal to noise ratio and contrast for the organs of interest (e.g., uterus, cervix and vagina). However, image datasets of lower quality maybe utilized, if needed, due to system hardware or other constraints. Since organs may shift over time, in most embodiments, the pre-operative imaging is performed immediately prior to the catheter insertion procedure itself with the patient under general anesthesia to prevent movement.

Figure 3:
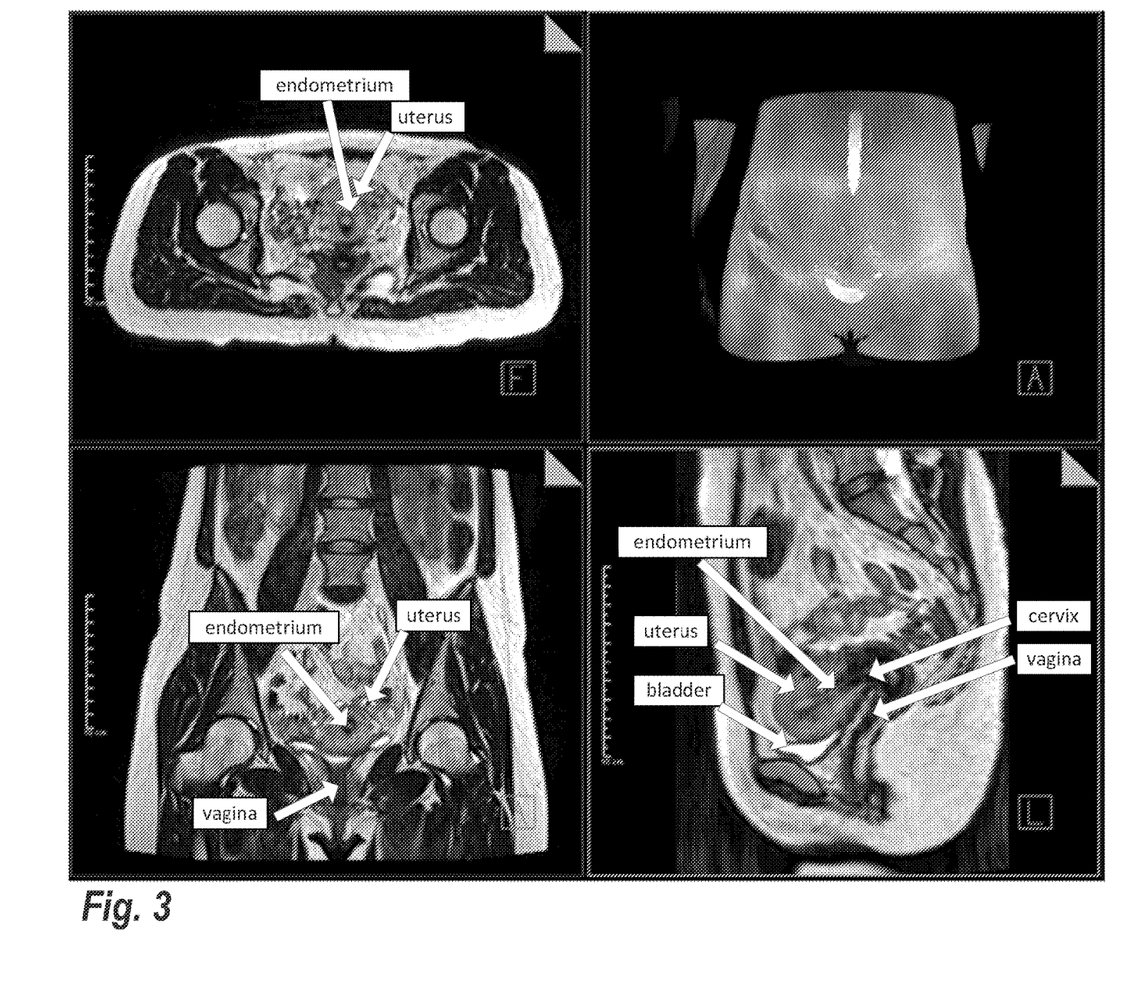
FIG. 3 shows a screen capture of a high resolution T2-weighted dataset of a female pelvis displayed using multi-planar reconstruction, as may be utilized in some embodiments.

The selected image dataset 210 is input into a segmentation algorithm performed at step 215 which identifies the relevant anatomical organs and landmarks in segmented data 220. Examples of anatomical organs and landmarks that may be identified at step 215 include, without limitation, the endometrium, the uterus, the vagina, the bladder, and the cervix. FIG. 3 shows a screen capture of a high resolution T2-weighted dataset of a female pelvis displayed using multi-planar reconstruction. Relevant anatomical structures are identified and would be segmented to reconstruct the anatomy through which the catheter will be inserted.

Various segmentation techniques generally known in the art may be used at step 215. In some embodiments, this segmentation is manual or semi-automatic and requires some input from an operator (e.g., radiologist) to aid in the identification of areas of interest on the image (e.g., via a drawing tool in a GUI). In other embodiments, the segmentation may be automatically performed, for example, using machine learning techniques. For example, an automated classification technique may be used to assign class labels to voxels in the selected image dataset 210 using a technique such as k-means, k-nearest neighbors, clustering decision trees, or an artificial neural network.

An anatomical model 225 is generated at step 222 from the segmented data 220. Effectively, the anatomical model 225 encompasses key organs related to the operation being performed. Thus, based on the segmented data 220, the structure of each organ is determined. This structure includes dimensions (e.g., length, width, height, etc.) and contours of the organ of interest. In some embodiments, surface features of each organ of interest may also be determined and represented in the anatomical model. The model is effectively a mathematical or visual representation of the segmented organ.

Using the anatomical model 225, an algorithm is performed at step 230 to predict the best location for implantation. This location, referred to herein as the "optimal implant location," is the region where the endometrium is considered to be the most receptive to implantation. Typically, the optimal implant location is in the top portion of the uterus between the subject's fallopian tubes. Various techniques generally known in the art may be applied for determining the optimal implant location. For example, in some embodiments, the locations of the subject's fallopian tubes are identified in the anatomical model 225. Then the algorithm performed at step 230 creates a "v" shape with an imaginary line extending from each fallopian tube. The intersection of the lines is the optimal implant location. In other embodiments, a midpoint between the internal cervix and the uterine fundus along a central axis is used as the optimal implant location.

The implant target point 235 is then combined at step 240 with the anatomical model 225 to create a 3D rendering 245 for guiding the procedure. The 3D rendering 245 may be produced using any technique generally known in the art including, without limitation, techniques such as raycasting, surface rendering (e.g., shaded surface rendering), volume rendering, etc. It is to be understood that the 3D rendering can be performing using a CPU in the central control unit 26 of FIG. 1 or by dedicated rendering hardware such as a graphics card or volume rendering card. In some embodiments, a plurality of graphical processing units (GPU) is used to perform the rendering in a distributed manner.

To visualize three dimensions of the area around the implant target point 235 on a two-dimensional display (e.g., display 40 of the operator interface in FIG. 1), an alpha compositing may be applied to the 3D rendering 245 whereby individual points of the 3D rendering 245 are assigned color values and opacity values. Each point of the 3D rendering 245 may be assigned a color value (e.g., a RGB value) and an alpha value to parameterize the opacity. In some embodiments, one or more illumination models may be used to assign a suitable color value. The illumination model may take into account light effects in a modeled or simulated irradiation of the implant target point 235 for the purposes of visualization. One or more illumination models generally known in the art may be used including, without limitation, a Phong, Gouraud or Schlick model.

In some embodiments, the 3D rendering 245 provides a mesh representation of the organs of interest included in the anatomical model 225, with the implant target point 235 highlighted. This highlighting may be performed, for example, by illuminating the implant target point 235 with a different color than the color used for the surrounding anatomy.

Following generation of the 3D rendering 245, real-time MR imaging is started. Real-time imaging is performed at step 250 (e.g., using the system 100 shown in FIG. 1) to produce a real-time MR image dataset 255. At step 260, the 3D rendered model 245 is fused or overlaid on the real-time images from the real-time MR image dataset 255 to produce combined dataset 265. Prior to step 260, the real-time MR image dataset 255 may be analyzed to detect the organs or landmarks of interest present in the segmented data 220 in order to aid in registration of the real-time MR image dataset 255 with the 3D rendered model 245 during the fusion (or overlaying) process.

Simultaneously, at step 270, the procedure of inserting the catheter into the endometrial cavity and navigating to the target implantation location may be performed. During the procedure, the combined dataset 265 is presented on a display viewable to the clinicians performing the implantation procedure. The catheter used during the procedure is designed to provide visibility in the combined dataset 265 during the procedure. For example, in some embodiments, the catheter includes resonant-frequency circuitry which tuned to the MRI frequency in order to make the catheter visible under MRI. In other embodiments, the catheter is marked at intervals with paramagnetic rings. Thus, using the combined dataset 265, the catheter may be guided through the endometrial cavity until it visually overlays the implant target point 235 at which point embryos in the catheter may be expelled into the region.

Figure 4:
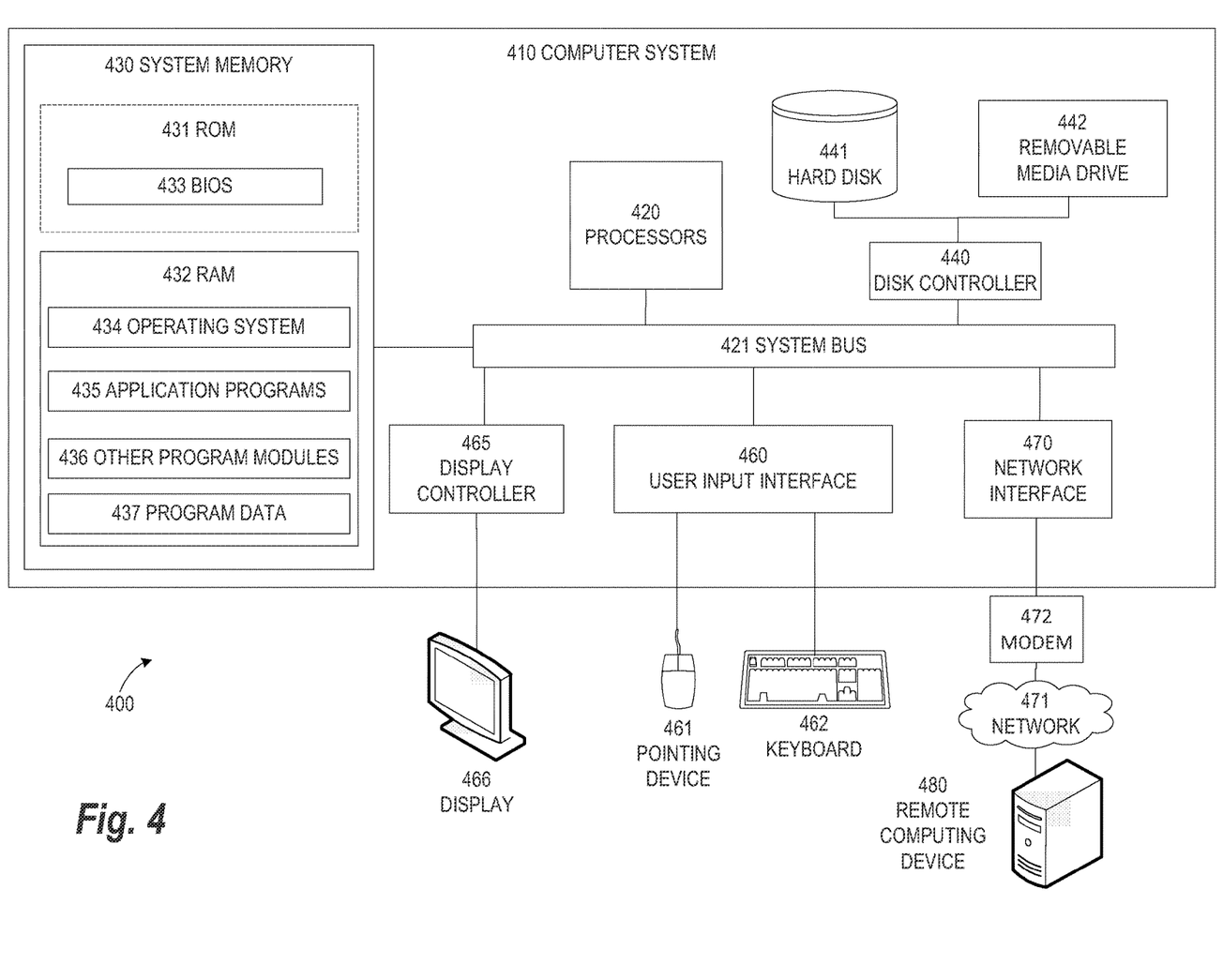
FIG. 4 illustrates an exemplary computing environment within which embodiments of the invention may be implemented.

FIG. 4 illustrates an exemplary computing environment 400 within which embodiments of the invention may be implemented. For example, this computing environment 400 may be used to implement the process 200 described in FIG. 2. In some embodiments, the computing environment 400 may be used to implement one or more of the components illustrated in the system 100 of FIG. 1. The computing environment 400 may include computer system 410, which is one example of a computing system upon which embodiments of the invention may be implemented. Computers and computing environments, such as computer system 410 and computing environment 400, are known to those of skill in the art and thus are described briefly here.

As shown in FIG. 4, the computer system 410 may include a communication mechanism such as a bus 421 or other communication mechanism for communicating information within the computer system 410. The computer system 410 further includes one or more processors 420 coupled with the bus 421 for processing the information. The processors 420 may include one or more central processing units (CPUs), graphical processing units (GPUs), or any other processor known in the art.

The computer system 410 also includes a system memory 430 coupled to the bus 421 for storing information and instructions to be executed by processors 420. The system memory 430 may include computer readable storage media in the form of volatile and/or nonvolatile memory, such as read only memory (ROM) 431 and/or random access memory (RAM) 432. The system memory RAM 432 may include other dynamic storage device(s) (e.g., dynamic RAM, static RAM, and synchronous DRAM). The system memory ROM 431 may include other static storage device(s) (e.g., programmable ROM, erasable PROM, and electrically erasable PROM). In addition, the system memory 430 may be used for storing temporary variables or other intermediate information during the execution of instructions by the processors 420. A basic input/output system (BIOS) 433 containing the basic routines that help to transfer information between elements within computer system 410, such as during start-up, may be stored in ROM 431. RAM 432 may contain data and/or program modules that are immediately accessible to and/or presently being operated on by the processors 420. System memory 430 may additionally include, for example, operating system 434, application programs 435, other program modules 436 and program data 437.

The computer system 410 also includes a disk controller 440 coupled to the bus 421 to control one or more storage devices for storing information and instructions, such as a hard disk 441 and a removable media drive 442 (e.g., floppy disk drive, compact disc drive, tape drive, and/or solid state drive). The storage devices may be added to the computer system 410 using an appropriate device interface (e.g., a small computer system interface (SCSI), integrated device electronics (IDE), Universal Serial Bus (USB), or FireWire).

The computer system 410 may also include a display controller 465 coupled to the bus 421 to control a display 466, such as a cathode ray tube (CRT) or liquid crystal display (LCD), for displaying information to a computer user. The computer system includes an input interface 460 and one or more input devices, such as a keyboard 462 and a pointing device 461, for interacting with a computer user and providing information to the processor 420. The pointing device 461, for example, may be a mouse, a trackball, or a pointing stick for communicating direction information and command selections to the processor 420 and for controlling cursor movement on the display 466. The display 466 may provide a touch screen interface which allows input to supplement or replace the communication of direction information and command selections by the pointing device 461.

The computer system 410 may perform a portion or all of the processing steps of embodiments of the invention in response to the processors 420 executing one or more sequences of one or more instructions contained in a memory, such as the system memory 430. Such instructions may be read into the system memory 430 from another computer readable medium, such as a hard disk 441 or a removable media drive 442. The hard disk 441 may contain one or more datastores and data files used by embodiments of the present invention. Datastore contents and data files may be encrypted to improve security. The processors 420 may also be employed in a multi-processing arrangement to execute the one or more sequences of instructions contained in system memory 430. In alternative embodiments, hard-wired circuitry may be used in place of or in combination with software instructions. Thus, embodiments are not limited to any specific combination of hardware circuitry and software.

As stated above, the computer system 410 may include at least one computer readable medium or memory for holding instructions programmed according to embodiments of the invention and for containing data structures, tables, records, or other data described herein. The term "computer readable medium" as used herein refers to any medium that participates in providing instructions to the processor 420 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 441 or removable media drive 442. Non-limiting examples of volatile media include dynamic memory, such as system memory 430. Non-limiting examples of transmission media include coaxial cables, copper wire, and fiber optics, including the wires that make up the bus 421. Transmission media may also take the form of acoustic or light waves, such as those generated during radio wave and infrared data communications.

The computing environment 400 may further include the computer system 410 operating in a networked environment using logical connections to one or more remote computers, such as remote computer 480. Remote computer 480 may be a personal computer (laptop or desktop), a mobile device, a server, a router, a network PC, a peer device or other common network node, and typically includes many or all of the elements described above relative to computer system 410. When used in a networking environment, computer system 410 may include modem 472 for establishing communications over a network 471, such as the Internet. Modem 472 may be connected to bus 421 via user network interface 470, or via another appropriate mechanism.

Network 471 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 410 and other computers (e.g., remote computer 480). The network 471 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 471.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A method for performing image-guided embryo transfer for in vitro fertilization, the method comprising:
performing a pre-operative magnetic resonance imaging (MRI) scan of a subject's pelvic region to yield a first MRI image dataset;
applying, by a computer, a segmentation routine to the first MRI image dataset to yield segment data;
creating, by the computer, an anatomical model of the subject's pelvic region using the segment data;
determining, by the computer, an optimal implant location based on the anatomical model;
creating, by the computer, a three-dimensional rendering of the optimal implant location based on the first MRI image dataset; performing a real-time MRI scan of the subject's pelvic region to yield a second MRI image dataset;
combining the second MRI image dataset with the three-dimensional rendering of the optimal implant location to yield a combined image dataset; and
presenting a display of the combined image dataset to guide insertion of a catheter into the subject's endometrial cavity for embryo transfer.

2. The method of claim 1, wherein an image fusion technique is used to combine the second MRI image dataset with the three-dimensional rendering of the optimal implant location.

3. The method of claim 1, further comprising:
presenting a visualization of the catheter on the display based on a radio frequency signal emitted by the catheter.

4. The method of claim 1, wherein the catheter comprises one or more paramagnetic rings and the method further comprises:
presenting a visualization of the catheter on the display based on a detection of the one or more paramagnetic rings.

5. The method of claim 1, wherein the three-dimensional rendering of the optimal implant location comprises a mesh centered at the optimal implant location.

6. The method of claim 5, wherein one or more voxels corresponding to the optimal implant location in the mesh are presented with a different color representation than other voxels included in the mesh.

7. The method of claim 5, wherein one or more voxels corresponding to the optimal implant location in the mesh are presented with a different opacity representation than other voxels included in the mesh.

8. An article of manufacture for performing image-guided embryo transfer for in vitro fertilization, the article of manufacture comprising a computer-readable, non-transitory medium holding computer-executable instructions for performing a method comprising:

receiving a first magnetic resonance imaging (MRI) image dataset representative of a subject's pelvic region acquired using a pre-operative MRI scan;

applying a segmentation routine to the first MRI image dataset to yield segment data;

creating an anatomical model of the subject's pelvic region using the segment data;

determining an optimal implant location based on the anatomical model;

creating a three-dimensional rendering of the optimal implant location based on the first MRI image dataset;

receiving a second MRI image dataset representative of the subject's pelvic region acquired using a real-time MRI scan;

combining the second MRI image dataset with the three-dimensional rendering of the optimal implant location to yield a combined image dataset; and presenting a display the combined image dataset to guide insertion of a catheter into the subject's endometrial cavity for embryo transfer.

9. The article of manufacture of claim 8, wherein image fusion technique is used to combine the second MRI image dataset with the three-dimensional rendering of the optimal implant location.

10. The article of manufacture of claim 8, wherein the method further comprises:

presenting a visualization of the catheter on the display based on a radio frequency signal emitted by the catheter.

11. The article of manufacture of claim 8, wherein the catheter comprises one or more paramagnetic rings and the method further comprises:

presenting a visualization of the catheter on the display based on a detection of the one or more paramagnetic rings.

12. The article of manufacture of claim 8, wherein the three-dimensional rendering of the optimal implant location comprises a mesh centered at the optimal implant location and the method further comprises:

applying a first color value to a first group of voxels corresponding to the optimal implant location in the mesh; and applying a second color value to a second group of voxels corresponding to voxels in the mesh not included in the first group, wherein the first color value and the second color value are distinct.

13. A system for performing image-guided embryo transfer for in vitro fertilization, the system comprising:

an imaging device comprising a plurality of coils configured to acquire a first magnetic resonance imaging (MRI) image dataset representative of a subject's pelvic region acquired using a pre-operative MRI scan a central control computer unit configured to:

apply a segmentation routine to the first MRI image dataset to yield segment data;

create an anatomical model of the subject's pelvic region using the segment data;

determine an optimal implant location based on the anatomical model;

create a three-dimensional rendering of the optimal implant location based on the first MRI image dataset; acquire a second MRI image dataset representative of the subject's pelvic region using a real-time MRI scan;

and the central control computer unit is further configured to: combine the second MRI image dataset with the three-dimensional rendering of the optimal implant location to yield a combined image dataset;

and present the combined image dataset on a display to guide insertion of a catheter into the subject's endometrial cavity for embryo transfer.

14. The system of claim 13, wherein the three-dimensional rendering of the optimal implant location comprises a mesh centered at the optimal implant location and the central control computer unit is further configured to:

apply a first color value to a first group of voxels corresponding to the optimal implant location in the mesh; and apply a second color value to a second group of voxels corresponding to voxels in the mesh not included in the first group, wherein the first color value and the second color value are distinct.

15. The system of claim 13, wherein the central control computer unit is further configured to:

presenting a visualization of the catheter on the display based on detection of one or more of a radio frequency signal emitted by the catheter and one or more paramagnetic rings on the catheter.

* * * * *